United States Patent [19]

Latham, Jr.

[11] 4,381,776
[45] May 3, 1983

[54] ANTICOAGULANT DISPENSING APPARATUS AND METHOD OF USE

[75] Inventor: Allen Latham, Jr., Jamaica Plain, Mass.

[73] Assignee: Haemonetics Corporation, Braintree, Mass.

[21] Appl. No.: 254,078

[22] Filed: Apr. 14, 1981

Related U.S. Application Data

[63] Continuation-in-part of Ser. No. 161,285, Jun. 20, 1980, abandoned.

[51] Int. Cl.$^3$ ........................ A61J 1/00; A61M 5/00
[52] U.S. Cl. ........................ 604/317; 128/DIG. 24; 604/408
[58] Field of Search ............... 128/334 R, 214, 214.2, 128/216, 272, 214 D, 272.1, 272.3, DIG. 24; 206/219; 224/461; 215/18 R; 222/81

[56] References Cited

U.S. PATENT DOCUMENTS

| | | | |
|---|---|---|---|
| 2,690,179 | 9/1954 | Fox | 128/216 |
| 3,696,919 | 10/1972 | DeWayne | 128/272.1 X |
| 3,856,138 | 12/1974 | Maekawa | 128/272 X |
| 3,977,555 | 8/1976 | Larson | 128/272 X |

Primary Examiner—Stephen C. Pellegrino
Attorney, Agent, or Firm—Hamilton, Brook, Smith & Reynolds

[57] ABSTRACT

An aseptically pure dispensing anticoagulant device adapted to be connected to a blood collection set and which may be aseptically treated by ethylene oxide or other high diffusivity sterilant without deleterious effects upon the anticoagulant. Various embodiments are shown; in one, a collapsible pouch is provided which includes a barrier against diffusion of water vapor and ethylene oxide. In another embodiment, a rigid anticoagulant container is employed which necessitates a secondary volume of air in a surrounding pouch to provide air to displace liquid in the rigid container as it passes into the set.

11 Claims, 6 Drawing Figures

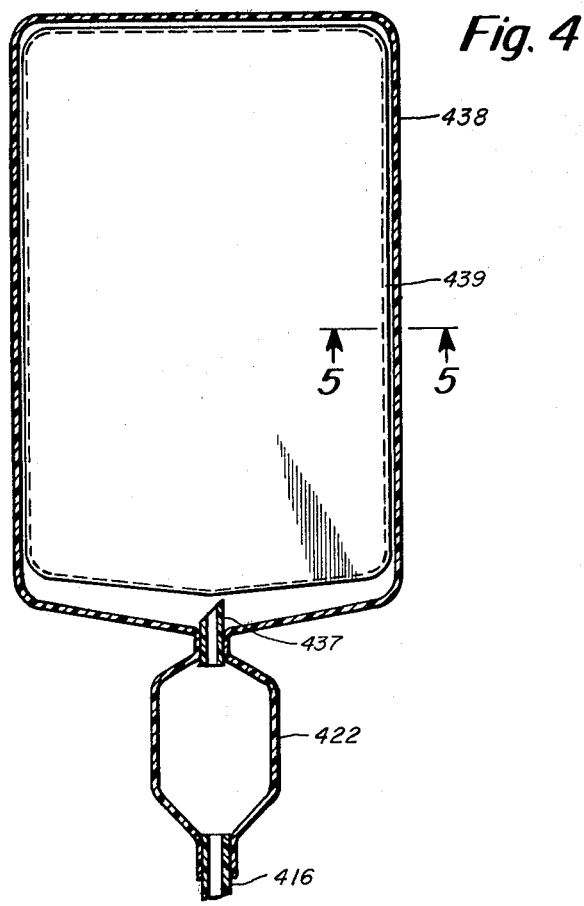
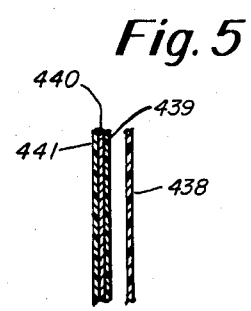

ANTICOAGULANT DISPENSING APPARATUS AND METHOD OF USE

DESCRIPTION

RELATED APPLICATIONS

This application is a continuation-in-part of Ser. No. 161,285 filed June 20, 1980, now abandoned.

BACKGROUND ART

In the collection of blood and, more particularly, human whole blood, it is desired that as soon as the blood is withdrawn from the donor that it be mixed with anticoagulant in order to prevent clotting. The anti-coagulant may be mixed in one of several ways. For example, as shown in U.S. Pat. No. 4,086,924, it may be mixed at the distal end of the phlebotomy needle, or as shown in U.S. Pat. No. 3,221,741, it may be simply collected in a sterile container, containing a predetermined amount of anticoagulant, such as an aqueous solution of citric acid, sodium citrate, and dextrose, commonly known as an A.C.D. solution. In the former apparatus, the anticoagulant is ratioed into the whole blood as it is drawn, and thus the anticoagulated whole blood which is withdrawn into the whole blood receiving bag always contains an acceptable concentration of anticoagulant. In the latter situation, wherein the whole blood is received in a container which already has the desired amount of anticoagulant for a complete donor donation, the ratio of anticoagulant to blood is initially very high, thus in some cases, causing damage called "anticoagulant shock" to the blood cells. Accordingly, the present invention is principally concerned with a blood donation system in which the anticoagulant is mixed with the donated whole blood in a predetermined ratio.

A customary method of sterilizing the anticoagulant containers and the whole blood containers and related tubing utilizes either pressure steam autoclaving or treatment with a high diffusivity sterilant such as, ethylene oxide, or a combination of both. While pressure steam autoclaving is suitable for sterilizing the anticoagulant containers and tubing, it is not desirable for use with empty whole blood flexible containers, since it can cause the containers to collapse and stick together and it leads to the problem of riding the container of condensed steam following sterilization. On the other hand, while ethylene oxide is suitable for the whole blood containers, it is not acceptable for sterilizing collapsible pouches with anticoagulant solution, inasmuch as the ethylene oxide reacts with the anticoagulant. In the past, therefore, it has been found necessary to use a combination of ethylene oxide for sterilizing the empty containers and a pressure steam autoclave has been used to sterilize the container with the anticoagulant. The two systems are then spliced together via conduits to form a complete set. This creates the possibility of introducing non-sterile organisms within the system during the splicing procedure.

DISCLOSURE OF THE INVENTION

In view of the above, a need exists for an aseptically pure dispensing anticoagulant device which is coupled to the blood collecting unit and wherein the entire unit may be aseptically treated by ethylene oxide. This invention, therefore, relates to a new and unique device and method for aseptically dispensing anticoagulant. The essential feature of the invention is to encapsulate the anticoagulant solution in a vapor-tight container which will be contained inside the plastic walls of the blood collection set. This will assure that the plastic walls of the blood collection set are not exposed to water vapor from the anticoagulant at any time during storage, and therefore, will retain the clarity of the plastic originally used in their manufacture. Also, inasmuch as the anticoagulant solution is within a vapor-tight container inside the plastic walls of the blood collection set, the blood collection set may be sterilized using ethylene oxide and because of the vaportight barrier around the anticoagulant, the ethylene oxide will not react with the anticoagulant. Two distinct different containers are shown as preferred embodiments of the encapsulation method for the anticoagulant. One consists of a collapsible pouch made from materials which provide both a barrier against diffusion of water vapor and a barrier against diffusion of ethylene oxide. The other embodiment comprises a rigid container made of a material which serves as a barrier to both water vapor and ethylene oxide. When a rigid form of anticoagulant container is employed, it is necessary to encapsulate a sufficient volume of air in the surrounding pouch to allow air to displace the liquid in the container as it passes into the set. There are several possible arrangements shown in the specification for such a container.

BRIEF DESCRIPTION OF THE DRAWINGS

FIG. 4 is a cross-sectional view of a further embodiment of the invention in which the exterior encapsulating bag and the interior anticoagulant container are both made of collapsible plastic.

FIG. 5 is a view taken along lines 5—5 in FIG. 4.

BEST MODE OF CARRYING OUT THE INVENTION

Figure 1:
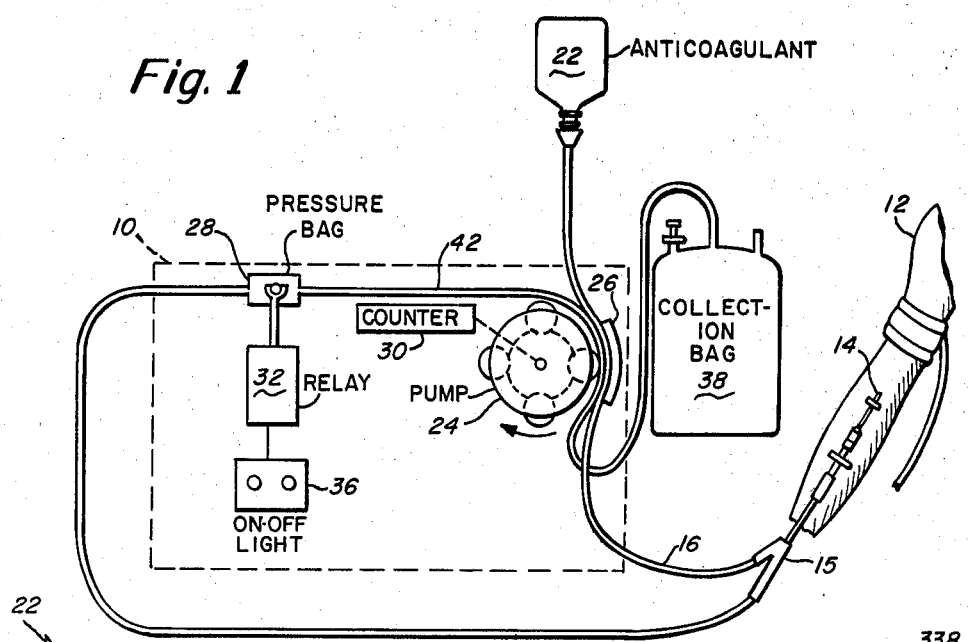
FIG. 1 is a diagramatic illustration of a blood donor system showing the location of the anticoagulant with respect to the collection bag.

The preferred embodiments of this invention can be described in more detail with reference to FIG. 1, which illustrates a typical blood donor system in which the anticoagulant dispenser of this invention may be utilized. FIG. 1 corresponds to FIG. 1 of copending U.S. Pat. application Ser. No. 182,510 filed on Aug. 29, 1980. The apparatus as shown in FIG. 1, which is of relevance to this invention, may be briefly described as follows. Anticoagulant from container 22 is supplied to a Y connector 15 on a phlebotomy needle 14 via tubing or conduit 16. The Y connector 15 is coupled on one side to the distal end of the phlebotomy needle 14. The other side of Y connector 15 is coupled to tubing 42 which passes through a sensing device 28 to a roller pump 24. After passing through the roller pump, conduit 42 is coupled to whole blood collection bag 38. Tubing or conduit 16 from the anticoagulant pouch is likewise passed through the rollers of pump 24. Pump 24 is a roller-type pump as described in U.S. Pat. No. 2,565,286, having a movable platen 26 which clamps tubing 18 and tubing 42 against the rollers of the pump when the platen is in its closed position.

Prior to making a venipuncture, phlebotomy needle 14 is primed with anticoagulant by opening platen 26 so that the rollers of the anticoagulant pump 24 do not apply their pumping pulses to tubing 16. With platen 26 in the open position, the outlet of anticoagulant pouch 22 is opened without interfering with the sterility of the system.

After venipuncture is made, the pump platen 26 is closed, thereby clamping tube 16 onto the rollers in pump 24 and initiating pumping action. Freshly withdrawn blood flows from the donor through tubing 42 into pressure bag 28 and thence to pump 24. Tubing 42 after it passes through pump 24 is connected to collector bag 38. The inner dimensions of tubing 16 is made smaller in proportion to the ratio desired of anticoagulant to whole blood. Thus, if the ratio desired is 8 to 1, the inner cross sectional area of the tubing 16 is made eight times smaller than the inner cross sectional area of tubing 42, and since both pass through the same rollers in pump 24, a uniform metering of anticoagulant to whole blood is achieved at the Y junction 15. This completes the general description of an overall blood donor system in which the anticoagulant dispenser of this invention may be utilized; it being understood that other applications for such dispensers may be found by those skilled in the art.

Figures 2, 3:
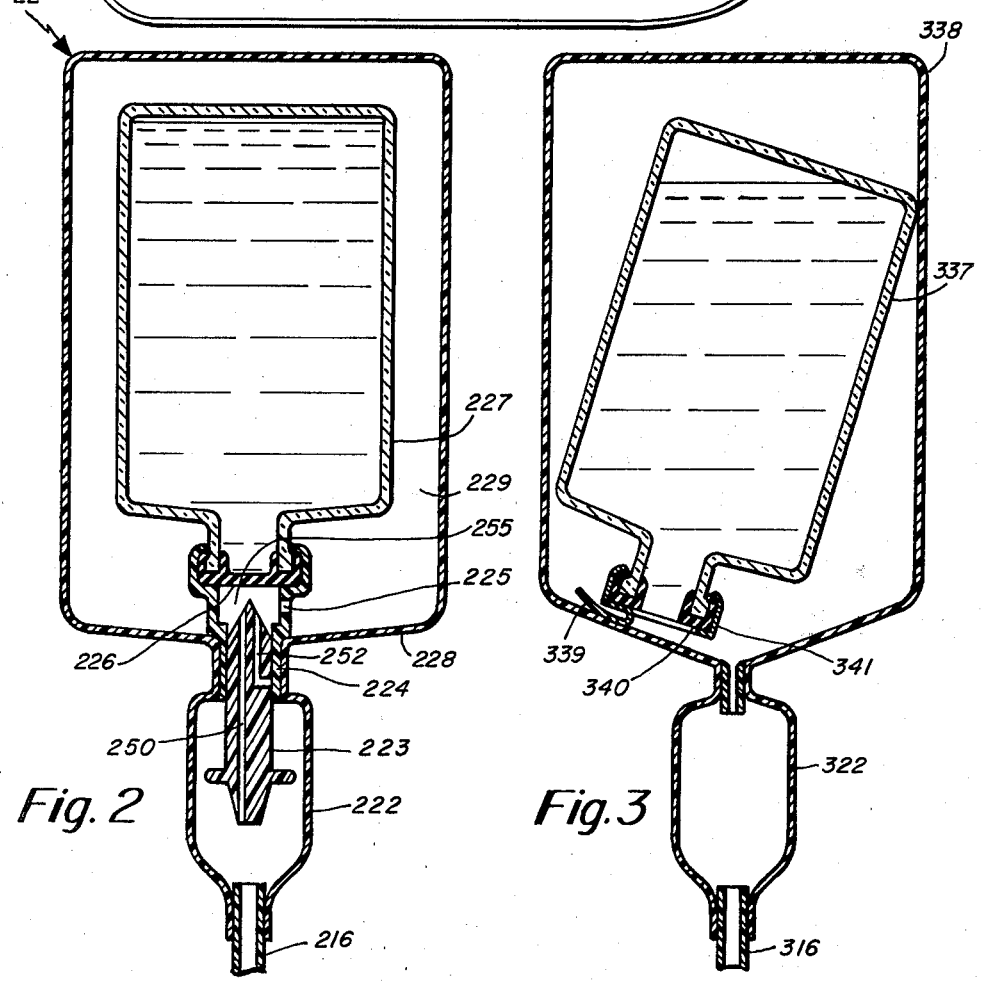
FIG. 2 is a cross-sectional view showing the details of an encapsulated rigid anticoagulant container of the invention.
FIG. 3 is a cross-sectional view of a further embodiment of the invention showing an encapsulated collapsible pouch within which is disposed a rigid anticoagulant container having a tear tab opening.

Referring now to FIG. 2, there is shown a specific embodiment of an anticoagulant dispenser 22 as used in the invention. In the apparatus of FIG. 2, an anticoagulant solution is contained in a rigid solution bottle 227, which has been previously sterilized using a steam pressure autoclave. The mouth of the container is closed by a puncturable closure 226 which may comprise aluminum foil or other readily puncturable closure means which is impermeable to moisture or air and, in particularly, to ethylene oxide. A rigid guide sleeve 224 is disposed coaxially about the outer periphery of the mouth of the solution bottle 227 in airtight relationship. A vented spike 223 is slidably disposed within guide sleeve 224 and adjacent the puncturable closure 226. The vented spike 223 may comprise a rigid plastic or hard rubber spike having a pointed end opposite the closure 226. A lengthwise slot or hole is provided in vented spike 223 at the location designated 250. This hole provides a passageway through spike 223 for flow of anticoagulant from the solution bottle 227 when the spike has pierced the closure 226. A shorter L-shaped fluid passageway 252 is provided on vented spike 223 having an opening into chamber 255 at one end and at the other end connecting to air passage 225 in guide sleeve 224. Thus, when the vented spike is inserted into the solution bottle an air passage between the air volume inside the collapsible pouch is provided through opening 225 and passageway 252 into the interior of the solution bottle. The air volume in space 229 between the solution bottle 227 and the collapsible pouch 228 should be made sufficiently large so as to permit the air in this volume to displace the liquid in the solution bottle as it passes into the set.

In operating the apparatus of FIG. 2, a technician manipulates vented spike 223 so as to penetrate the puncturable closure 226 of the bottle immediately before starting to use the solution. The vented spike has an air pathway 252 with a side opening to allow passage of air from the air volume, between the outside of the bottle and the inside of the collapsible pouch 228, through a small aperture 225 in an enlarged section 255 near the top of the guide sleeve 252, to the side opening of the air pathway in the spike. This then allows air to pass from the main air volume space 229 into the bottle 227 as solution is passing down the full length pathway 250 into the flexible drip chamber 222.

An important feature of the embodiment of FIG. 2 is the rigid guide sleeve 224 which is securely attached to the neck of the bottle by crimping the tip of the large end over the retainer 226 of the bottle closure. In this manner, the vented spike is kept well oriented so that the risk of accidental penetration of the wall of the collapsible pouch is eliminated.

FIG. 3 shows a further embodiment of the invention in which the solution bottle 227 of the previous embodiment is replaced by solution bottle 337 having a retainer 341 which may be made of non-corrosive metallic or plastic material which secures a rubber closure 340 over the mouth of the solution bottle 337. Tear tab 339 is provided on the retainer 341 which is sufficiently large to be grasped by a technician through the wall of the collapsible pouch 338 when it is the proper time to open the bottle. Thus, by removing or tearing away the retainer and allowing the rubber closure to slip out of the bottle, a solution within the bottle 337 is thereby allowed to drain out of the bottle while air from the air volume passes into the volume for displacement. It should be understood that the solution bottle has been previously sterilized in a steam autoclave before insertion in the collapsible pouch 338 and the pouch and bottle are then sterilized in an ethylene oxide solution as a complete entity. Thus, when the technician removes the retainer by stripping the tear tab 339 there is no possibility of contamination occurring in this process.

Also, as in FIG. 2, after the solution has been permitted to pass into the drip chamber, the pump platen 26 must be opened by the technician to permit delivery of the anticoagulant to the delivery tube 316.

FIG. 4 shows a further embodiment of the invention wherein the rigid inner container for the anticoagulant is replaced by a collapsible plastic-surface aluminum foil solution pouch 439. Both of the collapsible pouches 438 and 439 are made of suitable haemo compatible plastic materials such as polyurethane. The inner pouch 439 is made of a sandwich of materials which is shown more clearly in FIG. 5, to consist of an outer plastic layer 439 and an inner plastic layer 441 and sandwiched therebetween is a liner of aluminum foil 440. The aluminum acts as a vapor barrier to prevent interaction of the anticoagulant and the ethylene oxide during sterilization. It also assures that the plastic walls of the collapsible plastic outer pouch 438 and the remaining outer walls of the set are not exposed to water vapor from the anticoagulant at any time during storage and, therefore, these walls will retain the clarity of the plastic originally used in the manufacture. The lower end of the collapsible plastic-surface aluminum foil solution pouch 439 is provided with a burstable seal so that initiation of use of the solution is accomplished simply by squeezing the exterior of outer pouch 438 sufficiently hard to cause the seal to rupture. In the alternative, a simple squeezing tool might be provided for this purpose. Again, as in the previous embodiments, the collapsible inner solution pouch 439 may be sterilized by a steam autoclave after the container is filled with anticoagulant and prior to encapsulation within the plastic pouch 438. Following assembly and packaging of the entire set (a set being defined as the interconnecting plastic tube elements and anticoagulant and collection bags shown in FIG. 1), ethylene oxide sterilization is used in a conventional way to assure sterility throughout the interior of the set except for the anticoagulant itself which has already been sterilized by steam autoclaving while inside collapsible pouch 438.

Figure 6:
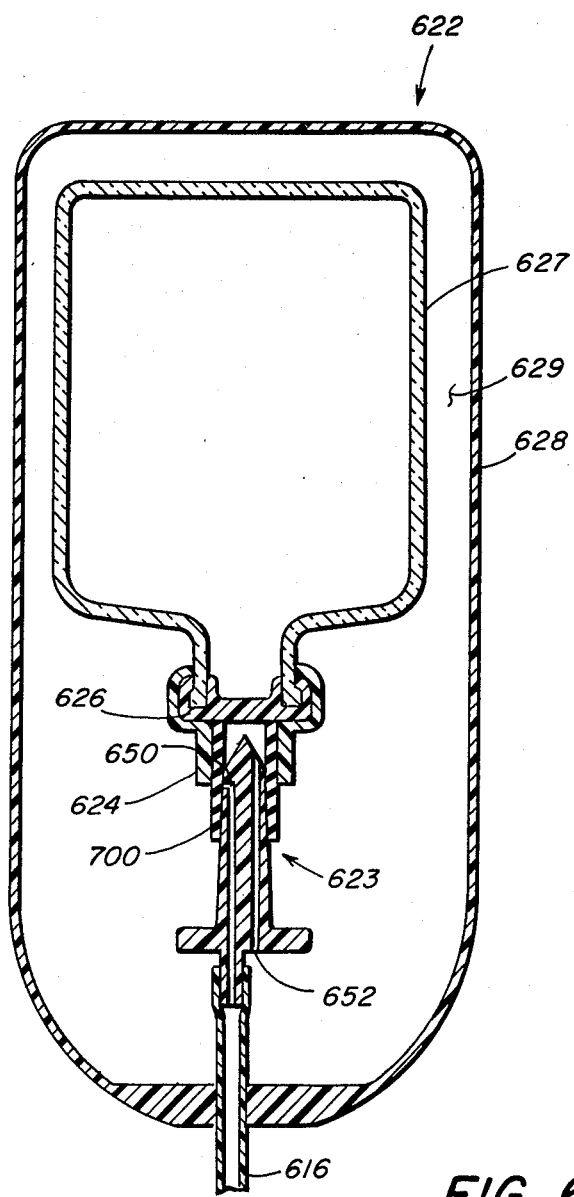
FIG. 6 is a cross-sectional view of a further embodiment of the invention.

The apparatus shown in FIG. 6 is an improved embodiment of the invention shown in FIG. 2. In the apparatus of FIG. 2, the air in the space 229 between the anticoagulant solution bottle and collapsible pouch 228 should be of sufficient volume to displace the liquid in the solution bottle as the solution passes into the set through tube 216 after vented spike 223 is inserted through closure 226. However, prior to insertion of spike 223, air in space 229 may escape into the set through aperture 225, pathway 250 and tube 216 unless means are provided to block this passageway. It is contemplated that valve means would be provided in tube 216 which would normally be closed to prevent air from escaping into the set and which would be manipulated open by the technician just prior to insertion of spike 223.

This is a cumbersome, non-automatic approach. Accordingly, the improvement described in FIG. 6 has been devised to obviate these difficulties.

Referring now to FIG. 6, a sterile anticoagulant dispenser 622 is shown consisting of an anticoagulant bottle 627 containing anticoagulant solution and a puncturable closure 626.

The dispenser 622 also includes a spike 623 mounted adjacent the closure 626 and an outlet tube 616 coupling the spike in fluid communication with an external software set, not shown. The external software set may consist of a standard plastic disposable blood collection bag (not shown).

A plastic collapsible pouch 628, totally encapsulating the spike 623 and bottle 627, completes the essential elements of the dispenser 622.

These elements are assembled as follows:

The bottle 627 with anticoagulant contained therein, is sealed by puncturable closure 626 and sterilized using a steam pressure autoclave. After sterilization, guide 624 with spike 623 and tubing 616 is coaxially mounted about the outer periphery of the mouth of the bottle and attached thereto. The pouch 628 is then placed over the entire assembly and heat sealed around the periphery in a conventional manner. The dispenser 622 with a conventional blood collection software set attached thereto may then be packaged and the interior of the set sterilized by ethylene oxide in a conventional way; it being understood that the ethylene oxide will not have a deleterious effect on the anticoagulant within the bottle.

An important element in the embodiment of FIG. 6, in contrast to the embodiment of FIG. 2 is spike 623. Spike 623 is slidably disposed within guide 624 and adjacent the puncturable closure 626. The spike 623 may comprise a rigid plastic or hard rubber spike having a pointed end opposite the closure 626. The spike is slightly tapered from the front end (spike end) to the back end, with the smaller outer diameter being closer to the spike end. A side-vented slot or hole 650 is provided in spike 623. This hole provides a passageway through spike 623 for flow of anticoagulant from the solution bottle 627 when the spike has pierced the closure 626. A second fluid passageway 652 is provided lengthwise along spike 623. Passageway 652 opens into air space 629 at the lower end of spike 623. Thus, when spike 623 is inserted into the solution bottle 627 an air passage between the air volume inside space 629 (between the collapsible pouch 628 and bottle 627) is provided through passageway 652 into the interior of the solution bottle. The air volume in space 629 is made sufficiently large so as to permit the air in this volume to displace the liquid in the solution bottle as it passes into the set through passageway 650 and tube 616.

Sleeve 700, in the form of a section of silicon rubber tubing is pressed onto the outside of spike 623 between guide 624 and the exterior tubular surface of spike 623. Sleeve 700 abuts closure 626 and may preferably be made integral with the closure to guarantee an airtight seal at this juncture. Prior to insertion of spike 623 into closure 626, the sleeve 700 is disposed as shown in FIG. 6 with resepct to spike 623 and thus maintains an airtight seal over the side port of passageway 650. Then, as spike 623 is forced into closure 626 to make a puncture, sleeve 700 is expanded (because of the slight taper of the external diameter of spike 623) thereby providing a gripping action within guide 624 helping to immobilize the spike 623 after the closure 626 is punctured and the spike 623 is in its operational position. Note that until shortly after the closure 626 is actually punctured, the side port entrance to passageway 650 is sealed by sleeve 700 and that prior to puncture of closure 626, air in space 629 cannot exit tube 616 since the side port of passageway 650 is sealed by sleeve 700.

The spike 623 may be moved so as to puncture the closure 626 by manually compressing the pouch 628 and pushing the spike or by pushing the bottle 627 down on the spike.

The embodiment of FIG. 6, as thus described, has the advantage that loss of air by way of the anticoagulant passageway 650 is prevented during storage and handling, and the anticoagulant passageway 650 is opened automatically during the process of pushing the spike 623 through the puncturable closure 626. By appropriate proportioning of the pouch 628 in the region of the spike 623, it will be readily possible to provide for positive pressure within the pouch 628 at the time that the spike 623 is being pushed through the puncturable closure 628. This is desirable because the air pressure will force anticoagulant into passageway 650 as soon as the opening to the passageway has passed through the puncturable closure, thus no solution will backflow through the air passage 652 causing loss of solution in the air chamber 629 of the bag, and flow of anticoagulant through passageway 650 will be initiated in a very positive manner.

Those skilled in the art will recognize many equivalents to the specific embodiments described herein. Such equivalents are considered part of this invention and are intended to be covered by the following claims.

I claim:
1. A blood collection set, comprising:
   a. an anticoagulant solution in a first rigid container impermeable to water vapor and sterilant;
   b. a blood receiving container;
   c. a second container, permeable to said sterilant, surrounding said first container;
   d. conduit means interconnecting said second container and said bag; and
   e. rupture means for rupturing the first container so that the anticoagulant solution may flow from said first container through the conduit means connecting the second container and said bag.

2. The apparatus of claim 1 in which a volume of air is provided between the first container and the second container, said volume of air being sufficiently large so as to displace the fluid anticoagulant solution in the first container.

3. The apparatus of claim 1 in which the rupture means comprises a rigid guide means secured to one end of said first rigid container and having a spike means slidably disposed within said rigid guide means.

4. The apparatus of claim 3 in which the rigid spike has a pair of passageways, one of which, when the spike has punctured the first rigid container, provides a passage for the flow of anticoagulant from the container to the conduit means, the other of which provides an air passage between the end of the spike nearest the first rigid container and a volume of air intermediate said first and second containers.

5. The apparatus of claim 4 having closure means for maintaining the anticoagulant passageway closed until the spike punctures the first rigid container.

6. The apparatus of claim 5 in which the closure means includes a sleeve provided coaxial to said spike and intermediate said guide means.

7. The apparatus of claim 6 in which the sleeve is adapted to expand within said guide means as said spike is slid toward said first rigid container in the act of puncturing the container.

8. The apparatus of claim 7 in whicn the sleeve abuts a puncturable portion of said rigid container.

9. A method of sterilizing the equipment necessary for drawing blood and mixing the blood with an anticoagulant comprising the steps of:

(a) sterilizing an integral anticoagulant container of material impermeable to high diffusivity sterilant by a high temperature steam autoclave process;
(b) connecting puncture means between said anticoagulant container and a second container;
(c) encapsulating said integral anticoagulant container and puncture means within said second container comprising flexible, compressable, material;
(d) connecting conduit means from a phlebotomy needle to said second container; and
(e) connecting conduit means from said phlebotomy needle to a whole blood collecting bag.

10. The method of claim 9 including the additional step of: sterilizing the interior of the equipment with high diffusivity sterilant after the sterilized anticoagulant container has been encapsulated in the second container.

11. A blood collection set, comprising:
a. an anticoagulant solution in a first container impermeable to water vapor and sterilant, said first container comprising a foil lined plastic pouch;
b. a blood receiving container;
c. a second plastic bag container, permeable to said sterilant, surrounding said first container;
d. conduit means interconnecting said second container and said blood receiving container, and
e. rupture means intermediate said first container and said conduit means to rupture the first container so that the anticoagulant solution may flow from said first container to the conduit means connecting the second container and said blood receiving container.

* * * * *